United States Patent
Hodge et al.

(10) Patent No.: US 8,267,922 B2
(45) Date of Patent: Sep. 18, 2012

(54) PHOTOTHERAPY LIGHT WITH DUAL SPRING SUPPORT NECK

(75) Inventors: Colin G. Hodge, Ellicott City, MD (US); Michael H. Mackin, Ellicott City, MD (US)

(73) Assignee: General Electric Company, Schenectady, NY (US)

( * ) Notice: Subject to any disclaimer, the term of this patent is extended or adjusted under 35 U.S.C. 154(b) by 1198 days.

(21) Appl. No.: 11/405,231

(22) Filed: Apr. 17, 2006

(65) Prior Publication Data
US 2007/0244525 A1    Oct. 18, 2007

(51) Int. Cl.
*F21S 8/08*    (2006.01)

(52) U.S. Cl. .......... 606/1; 607/88; 607/90; 607/91; 362/12; 362/39; 362/130; 362/217; 392/383; 606/2; 606/19

(58) Field of Classification Search .......... 607/88–94; 362/12, 418, 39, 217, 130; 392/383; 606/2–19; 128/898
See application file for complete search history.

(56) References Cited

U.S. PATENT DOCUMENTS

| | | | |
|---|---|---|---|
| 1,790,500 A | | 1/1931 | Fischer |
| 2,607,881 A | * | 8/1952 | Anderson ............ 362/144 |
| 2,832,157 A | * | 4/1958 | Hudson ............ 34/90 |
| 3,666,938 A | * | 5/1972 | Dolega ............ 362/398 |
| 4,698,068 A | * | 10/1987 | Jensen ............ 44/507 |
| 4,809,677 A | * | 3/1989 | Mackin et al. ............ 600/22 |
| 5,008,793 A | * | 4/1991 | Copeland ............ 362/413 |
| 5,339,223 A | * | 8/1994 | Kremenchugsky et al. .. 362/572 |
| 5,851,212 A | * | 12/1998 | Zirps et al. ............ 606/167 |
| 5,915,072 A | * | 6/1999 | Campbell et al. ............ 392/418 |
| 5,924,681 A | * | 7/1999 | Bullard ............ 267/89 |
| 6,102,920 A | * | 8/2000 | Sullivan et al. ............ 606/147 |
| 6,253,380 B1 | * | 7/2001 | Larsson et al. ............ 2/114 |
| 6,290,713 B1 | * | 9/2001 | Russell ............ 607/88 |
| 6,402,681 B1 | * | 6/2002 | McDonough et al. ............ 600/22 |
| 6,413,205 B1 | * | 7/2002 | Finny ............ 600/22 |

(Continued)

FOREIGN PATENT DOCUMENTS
EP    0 627 243 A1    7/1994
(Continued)

OTHER PUBLICATIONS

Specification Sheet, GE Healthcare, Giraffe Spot PT Lite (2004).

*Primary Examiner* — Aaron Roane
(74) *Attorney, Agent, or Firm* — Andrus, Sceales, Starke & Sawall, LLP (57) ABSTRACT

A phototherapy light device for directing light onto an infant. The phototherapy light device has a base containing an illumination source and a gooseneck type of elongated neck that extends outwardly from the base and has a distal end adapted to be positioned to direct the light onto the infant. An optical fiber transmits the light from the illumination source to the distal end through the optical fiber where the light is passed through a light emanating device located at the distal end of the elongated neck. The elongated neck has two flexible sections, one of which has two coaxial springs to provide flexibility in positioning as well as to impart sufficient strength and rigidity to the elongated neck. The dual spring concept provides a system having reduced stresses while creating a double fault structural system without compromising the flexibility of the elongated neck.

11 Claims, 5 Drawing Sheets

U.S. PATENT DOCUMENTS

| | | | |
|---|---|---|---|
| 6,523,984 B2 * | 2/2003 | Belfer | 362/551 |
| 6,698,044 B2 * | 3/2004 | Greenfield et al. | 5/624 |
| 7,219,700 B2 | 7/2006 | Matsuyama | |
| 7,357,811 B2 * | 4/2008 | Dykes et al. | 607/90 |
| 2004/0039428 A1 * | 2/2004 | Williams et al. | 607/91 |
| 2005/0090879 A1 * | 4/2005 | Dykes et al. | 607/96 |
| 2006/0077672 A1 * | 4/2006 | Schaak | 362/418 |
| 2006/0098961 A1 * | 5/2006 | Seutter et al. | 392/383 |
| 2006/0195165 A1 * | 8/2006 | Gertner et al. | 607/86 |
| 2006/0221604 A1 * | 10/2006 | Martin et al. | 362/191 |
| 2006/0278816 A1 * | 12/2006 | Booty | 250/221 |

FOREIGN PATENT DOCUMENTS

JP                 106093      3/1989

* cited by examiner

PHOTOTHERAPY LIGHT WITH DUAL SPRING SUPPORT NECK

BACKGROUND

The present invention relates to a phototherapy light for treating infants and, more particularly, to a phototherapy light having an improved support system.

Hyperbilirubinemia is an affliction of newborn infants typified by an elevated level of a toxic molecule known as bilirubin in the infant's blood. Current medical therapy for such affliction is through the use of phototherapy where light radiation, generally within a certain wavelength band is directed upon the infant's skin.

There are a number of means or devices that are conventionally employed to direct the light upon the skin of the infant, one of which is to provide a bank of lights that are portable or can be built into an infant care apparatus and which direct the light radiation toward the infant positioned on an infant platform as a part of that apparatus.

Another means of providing phototherapy is through the use of a fiberoptic pad that is comprised of woven optical fibers such that the light radiation couples out of the optical fibers at the various bends that are formed in the optical fibers during the weaving process.

A still further means or device is by the use of a "gooseneck" phototherapy device that has a maneuverable, elongated neck that the caregiver can bend to the desired position to direct the light radiation upon the area of the infant where the light radiation is needed.

With the "gooseneck" type of phototherapy device, the distal end is positioned so as to direct the light radiation upon the infant and, in use, the distal end actually may be located over the infant in order to provide the needed light for phototherapy. As such, in that orientation the base is considerably remote from the distal end and yet the base supports that distal end and the elongated neck mounted therebetween in a cantilever manner extending outwardly from the base. The result is that the relatively high weight that is suspended over the infant requires substantial components of the phototherapy device to support the optical system adequately.

A difficulty, therefore, in the use of the gooseneck type of phototherapy light device, is that the flexibility and maneuverability of the distal end, as well as the elongated neck are important to facilitate the positioning of the distal, light emanating end at the desired location proximate to the infant and yet it is certainly important that the support for the distal end be sufficiently strong to guard against failure of the elongated neck that could result in the distal end sagging downwardly so as to potentially contact the infant. Since the light emanating, distal end can be at an elevated temperature, the contact with the infant is obviously not desirable and can cause harm to the infant.

At the present, there is provided a single pre-stressed helical spring that comprises a flexible section of the elongated neck in order to allow the user to position the distal end of the device at the desired location with respect to the infant. There are, however, certain difficulties with the use of a single helical spring. Among those difficulties are that the single spring has a high weight, is highly stressed and is a single fault system that upon failure, will inevitably result in the distal end dropping or sagging downwardly and thus having the potential of contacting the infant. The result is that the high stresses needed within the single internal support spring create low safety factors and single fault failure conditions in view of the relatively large mass suspended over the infant.

It would be advantageous to have a design and construction of a "gooseneck" type of phototherapy device that provides the necessary support for the distal end of the device but having reduced stresses and thereby increasing the safety factor so as to reduce the failure potential of the elongated neck and the potential downwardly movement of the distal end of the device.

SUMMARY OF THE INVENTION

Accordingly, the present invention relates to a phototherapy light device that is usable in the treatment of bilirubinemia of an infant. With the device of the present invention, the device preferably has a base that provides a foundation for the device. Extending from the base is an elongated "gooseneck" type of flexible neck that terminates at a distal end. Within the base, there is a light producing device, such as a light bulb, for the light therapy. The elongated neck encloses a light pipe or optical fiber system that transmits the light from the light source in the base to the distal end where a light emanating device is located to direct the light to impinge upon the infant. In an alternative embodiment, the light producing device may be located at the distal end of the elongated neck.

As used herein, the terms distal and proximal will be referred to in defining the location of the various components that are assembled to make up the present phototherapy light device of the present invention, that is, the proximal direction will be referred to as being toward the fixed base of the device while the distal direction will be referred to as toward the cantilever or light emanating end of the device.

By means of the flexibility of the elongated neck, the location of the distal end can be manipulated by the user to direct the light upon the desired area of the infant while the base remains in a stationary position.

The light emanating from the distal end of the optical fiber radiates somewhat outwardly in a diverging pattern by a lens where the light is directed outwardly from a housing to impinge upon the infant. The construction and operation of an embodiment of the lens and the overall assembly details of an exemplary distal end of the elongated neck is shown and described in co-pending U.S. patent application Ser. No. 11/327,554 entitled PHOTOTHERAPY LIGHT WITH FRESNEL LENS, filed Jan. 6, 2006 and owned by the present assignee and the disclosure of that pending patent application is hereby incorporated herein by reference in its entirety.

With the present invention, however, the elongated neck is specially constructed in order to sustain the weight of the distal end and extends from the base to the distal end of the phototherapy device. At least a portion of the elongated neck comprises a flexible section having an inner coil spring and an outer coil spring. The outer coil spring is an extension spring that is preloaded and encircles the inner coil spring such that the two springs are generally in a coaxial orientation. As such, the flexible section is strengthened by the presence of the two coaxial coil springs so that the elongated neck can fully support the distal end of the elongated neck and prevent the distal end of the elongated neck from sagging downwardly where it could contact an infant.

By the use of the coaxial dual springs, the outer spring can be only lightly pre-loaded as opposed to the prior art single spring that was heavily loaded. In addition, the employment of dual springs creates a double fault structural system which does not compromise the needed flexibility of the elongated neck, or ergonomics, and which allows the inner spring to support the distal end of the phototherapy device in combination with the outer spring.

In an exemplary embodiment, the elongated neck has a distal flexible section and a proximal flexible section. The proximal flexible section has the dual spring configuration while the distal flexible section may comprise only an inner spring. The proximal flexible section can be directly affixed to the base and there can be an intermediate tubing that is located between the proximal flexible section and the distal flexible section. A distal tubing thereupon extends for the distal flexible section to the distal end where the light emanating device is located.

As a further advantageous feature of the present invention, the coaxial spring arrangement is constructed by means of an outer spring assembly having end fittings and the outer spring assembly is dimensioned so as to be slidably affixed over the inner spring so that the outer spring assembly can be readily assembled to form the elongated neck and, just as easily, the outer spring assembly can be readily removed at the proximal end of the elongated neck for replacement thereof. As such in the event of a failure of either of the outer or inner springs, the other spring can be retained and only the failed spring replaced.

These and other features and advantages of the present invention will become more readily apparent during the following detailed description taken in conjunction with the drawings herein.

DETAILED DESCRIPTION OF THE INVENTION

Figure 1:
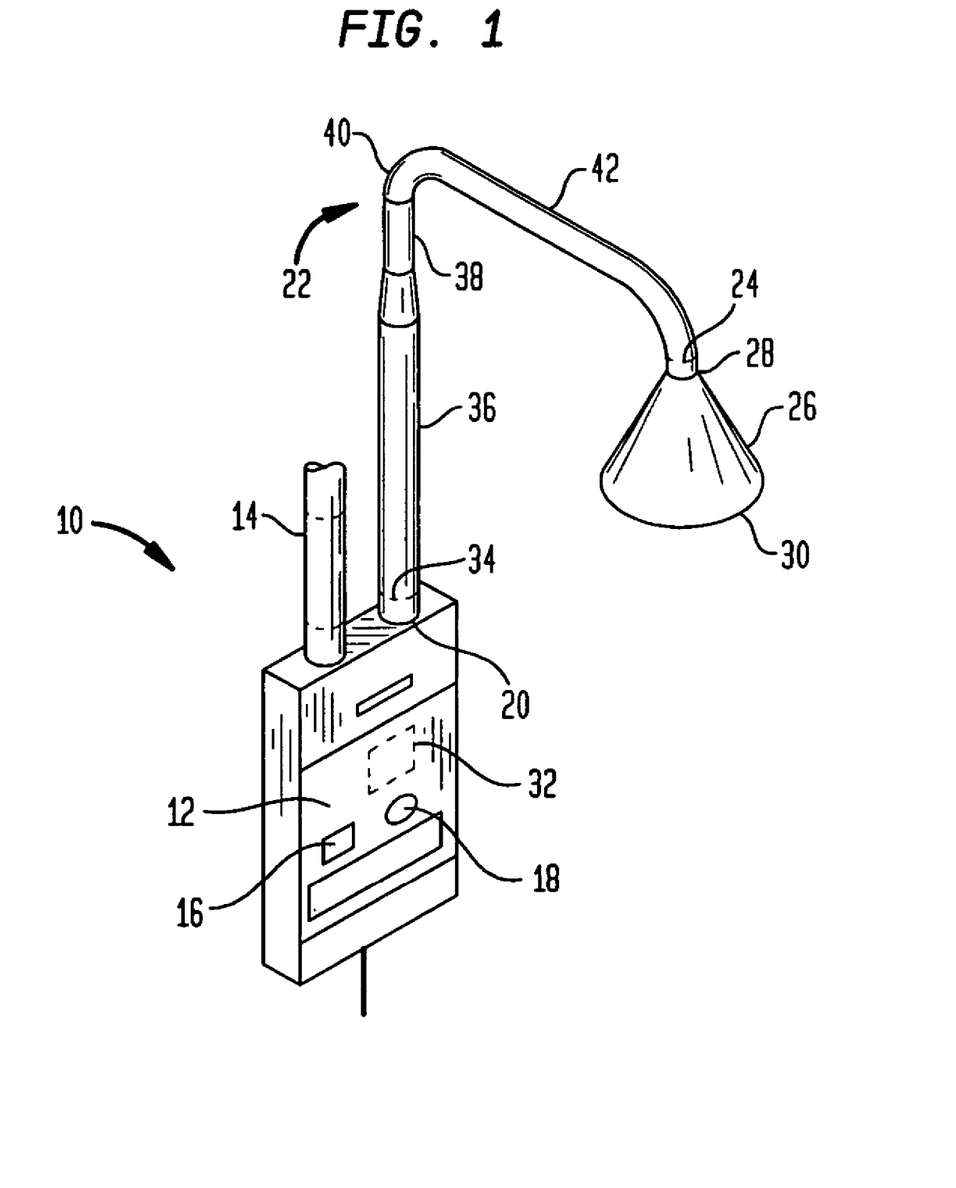
FIG. 1 is a perspective view of a phototherapy light device constructed in accordance with the present invention.

Referring now to FIG. 1, there is shown a perspective view of the phototherapy light device 10 constructed in accordance with the present invention. As can be seen, the phototherapy light device 10 includes a base 12 and, in the embodiment shown, the base 12 can be mounted to a stand 14 so that the phototherapy light device 10 can be moved to a location proximate to an infant for use in administering phototherapy. As an alternative, the base 12 can be affixed to an infant care apparatus, such as an incubator or infant warmer or may be physically incorporated into an infant care apparatus.

There can be suitable controls on the base 12, including a power switch 16 and an intensity control 18 to allow the user to set a desired intensity of the phototherapy light device directed onto an infant. In the upper surface of the base 12 there is an opening 20 where an elongated neck 22 is affixed to the base 12.

The elongated neck 22 itself is manipulatable by a user such as typical of a gooseneck lamp so that the user can position the elongated neck 22 as desired in order to position the distal end 24 of the elongated neck 22 in a particular location to direct the phototherapy light at a selected area of the infant. Affixed to the distal end 24 of the elongated neck 22 is a shade assembly 26 that is generally conical shaped with a reduced diameter proximal end 28 and a larger diameter distal end 30.

Thus, overall, there is an light source 32 located in the base 12 and which provides the light that is emitted from a light emanating device located at the distal end 30 of the shade assembly 26 to impinge upon the infant. As is conventional, the light source 32 can be a light bulb, for example, of about 50 watts, that provides light at the preferred wavelength to alleviate the bilirubinemia.

The elongated neck 22 is comprised of a number of components. As can be seen the proximal end 34 of the elongated neck 22 is affixed to the base 12 and there is a proximal flexible section 36 located at or adjacent to that proximal end 34 and the specific construction and assembly of that proximal flexible section 36 will be later explained. Extending distally from the proximal flexible section 36 is an intermediate tubing 38 that joins the proximal flexible section 36 to a distal flexible section 40. Extending distally from the distal flexible section 40 is a curved distal tubing 42 that extends to the distal end 24 of the elongated neck 22 so as to be conveniently locatable at a desired orientation with respect to an infant.

Figure 2:
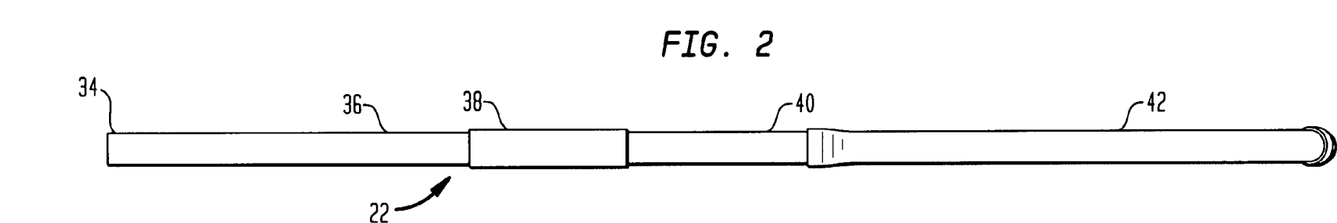
FIG. 2 is a top view of an elongated neck constructed in accordance with the present invention.

Turning now to FIG. 2, there is shown a top view of the elongated neck 22 constructed in accordance with the present invention and, in particular, there can be seen, the proximal end 34, the proximal flexible section 36, the intermediate tubing 38, the distal flexible section 40 and the curved distal tubing 42.

Figures 3, 4A, 4B, 4C:
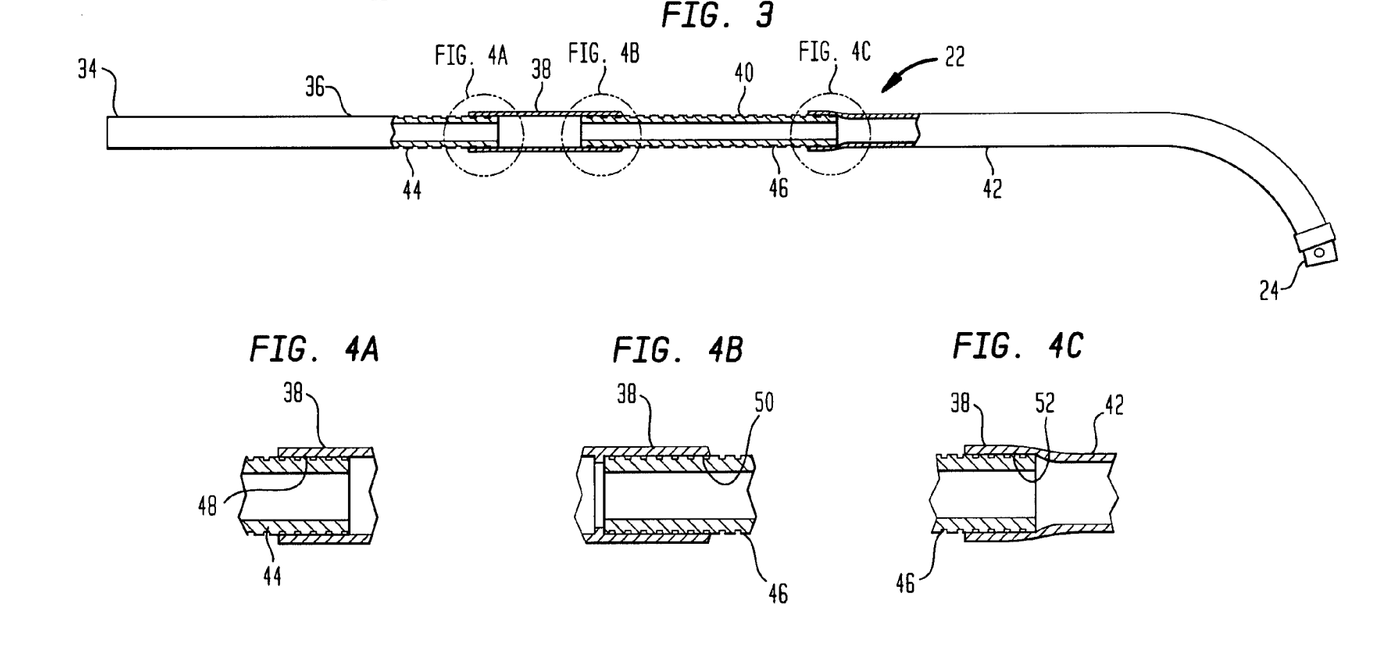
FIG. 3 is a side view of the elongated neck of FIG. 2.
FIGS. 4A, 4B and 4C are cross sectional views illustrating certain areas of the elongated neck designated as 3A, 3B, and 3C on FIG. 3.

Turning next to FIG. 3, taken along with FIG. 2, there can be seen a proximal inner spring 44 and a distal inner spring 46. Both the proximal and distal inner springs 44, 46 are of the type used in gooseneck lamps, that is, the proximal and distal inner springs 44, 46 can be distended or bent and will remain at the distended position so that the elongated neck 22 can be manipulated to a desired position and remain at that orientation. As such the elongated neck 22 can be bent at both of the locations of the proximal and distal inner springs 44, 46 i.e. the proximal flexible section 36 and the distal flexible section 40.

In FIGS. 4A, 46 and 4C, there are cross sectional views taken at the locations indicated as 3A, 3B and 3C of FIG. 3 and illustrating the mounting of the proximal and distal inner springs 44, 46. Thus, in FIG. 4A, the distal end of the inner spring 44 can be seen fitting into an inner socket 48 formed in the proximal end of the intermediate tubing 38 and is preferable adhesively bonded thereto. In FIG. 4B, there can be seen the proximal end of the distal inner spring 46 that is located within and preferably adhesively bonded to an inner socket 50 formed in the distal end of the intermediate tubing 38.

Next, in FIG. 4C, there is an illustration of the distal end of the distal inner spring 46 that is located within, and preferably adhesively bonded to an inner socket 52 formed at the proximal end of the distal tubing 42. In summary, therefore, the intermediate tubing 38 spans between and is adhesively bonded to the distal end of the proximal inner spring 44 and the proximal end of the distal inner spring 46 wherein the distal end of the distal inner spring 46 is adhesively bonded to the proximal end of the distal tubing 42.

Figure 5:
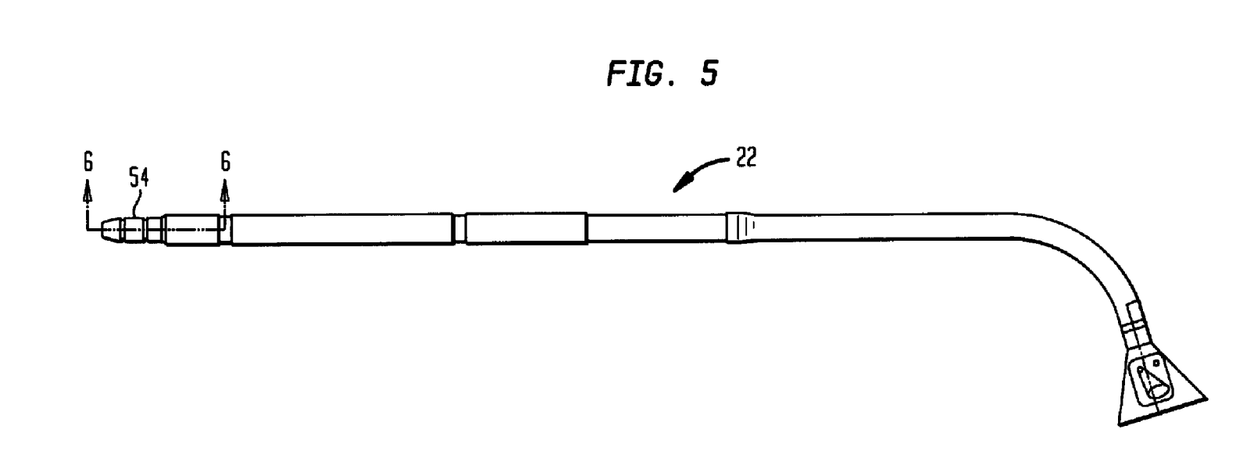
FIG. 5 is a side view of the of the elongated neck with the end fitting affixed thereto.
Figure 6:
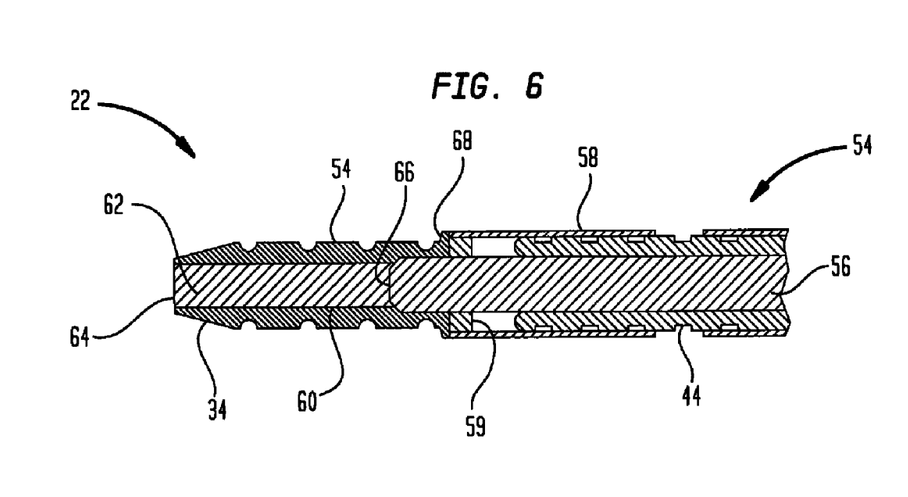
FIG. 6 is a cross sectional view of the end fitting shown in FIG. 5 and taken along the line 6-6 of FIG. 5.

Turning now to FIG. 5, there is shown a further side view of the elongated neck 22 having an inner fitting 54 that is used to connect the elongated neck 22 to the base 12 (FIG. 1). In FIG. 6, taken along with FIG. 5, there is an enlarged cross sectional view of that inner fitting 54 and illustrating the proximal end 34 of the elongated neck 22 where there can be seen the optical fiber 56 that transmits the light from the light source 32 (FIG. 1) to the optical fiber 56, through the elongated neck 22 to the light emanating device located in the shade assembly 26 (FIG. 1).

As such, in FIG. 6, the optical fiber 56 is shown located generally coaxially within the proximal inner spring 44. Along the outer surface of the proximal inner spring 44 is a protective sleeve 58 that encloses and contains any debris that may be created by the flexure of the proximal inner spring 44 and to prevent that debris from migrating outwardly. The protective sleeve 58 is, in the illustrated embodiment, a heat shrink sleeve. There is also a foam washer 59 to prevent the debris from migrating axially away from the proximal inner spring 44 toward the inner fitting 54. The proximal inner spring 44 can be adhesively affixed within the inner fitting 54.

The inner fitting 54 has an inner cylindrical bore 60, within which there is located a quartz member 62 having a proximal end 64 that receives the light from the light source 32 (FIG. 1) and a distal end 66 that abuts against the proximal end of the optical fiber 56 to transmit that light to the optical fiber 56. The proximal end of the optical fiber 56 is bonded to the inner cylindrical bore 60, again preferably by means of an adhesive. The inner fitting 54 reduces in diameter towards the proximal end 34 of the elongated neck 22, thereby forming a shoulder 68, the purpose of which will be later explained.

Figure 7:
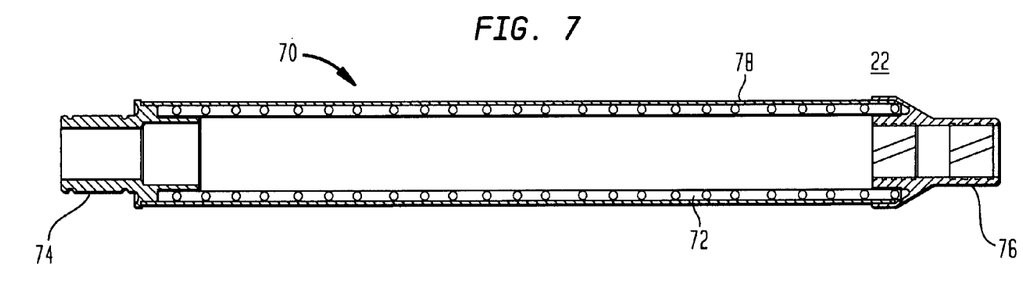
FIG. 7 is a cross sectional view of the outer spring assembly of the present invention.

Turning now to FIG. 7, there is shown a cross section view of an outer spring assembly 70 that is used to complete the elongated neck 22 by being located just external to and coaxial with the proximal inner spring 44 (FIG. 6). The outer spring assembly 70 comprises an outer spring 72 having a proximal fitting 74 and a distal fitting 76. Surrounding the exterior surface of the outer spring 72 is a cover sleeve 78 that provides a barrier to the migration of debris generated by the flexing of the outer spring 72 as well as to provide a good appearance to the overall device. The cover sleeve 78, as will be seen, is normally adhesively adhered to the proximal and distal fittings 74, 76 as is the outer spring 72. The outer spring is an extension spring that is preloaded so as to keep the elongated neck 22 in its position if there is some failure. The design of the outer spring 72 is dependent upon various factors, including the length of the spring, its internal stress level, the wire size, effect of corrosion, wear and the like.

Figure 8:
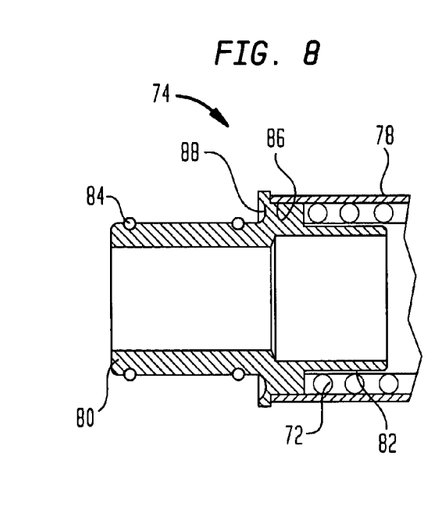
FIGS. 8 and 8A are enlarged cross sectional views of the end fittings usable with the outer spring assembly of FIG. 7.

Turning to FIG. 8, taken along with FIG. 7, there is a cross sectional view of the proximal fitting 74 and, as can be seen, the proximal fitting 74 includes a cylindrical proximal end 80 and a distally extending cylindrical flange 82. The proximal end 80 is adapted to be plugged into the base 12 (FIG. 1) and has a pair of O-rings 84 so as to fit with a close fitting within the base 12. The proximal end of the outer spring 72 is affixed to the cylindrical flange 82, preferable by an adhesive and the cover sleeve 78 is also affixed to the proximal fitting 74 at an outer flange 86 and, again, preferable by means of an adhesive. As a further feature of the proximal fitting 74, there is a shoulder 88 formed that faces proximally and the purpose of which will be later explained.

Figure 8A:
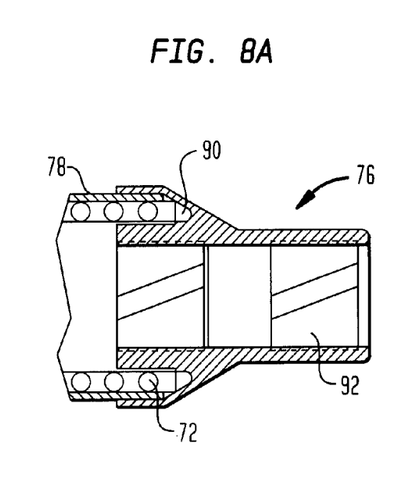

Turning now to FIG. 8A, taken along with FIG. 7, there is a cross sectional view of the distal fitting 76 and, with this distal fitting 76, the outer spring 72 as well as the cover sleeve 78 are affixed, preferably by adhesive bonding, within an annular opening 90 formed in the distal fitting 76. The distal fitting 76 also has an internal opening 92 formed therein having a predetermined internal diameter and the purpose of that internal opening 92 will be later explained.

Figure 9:
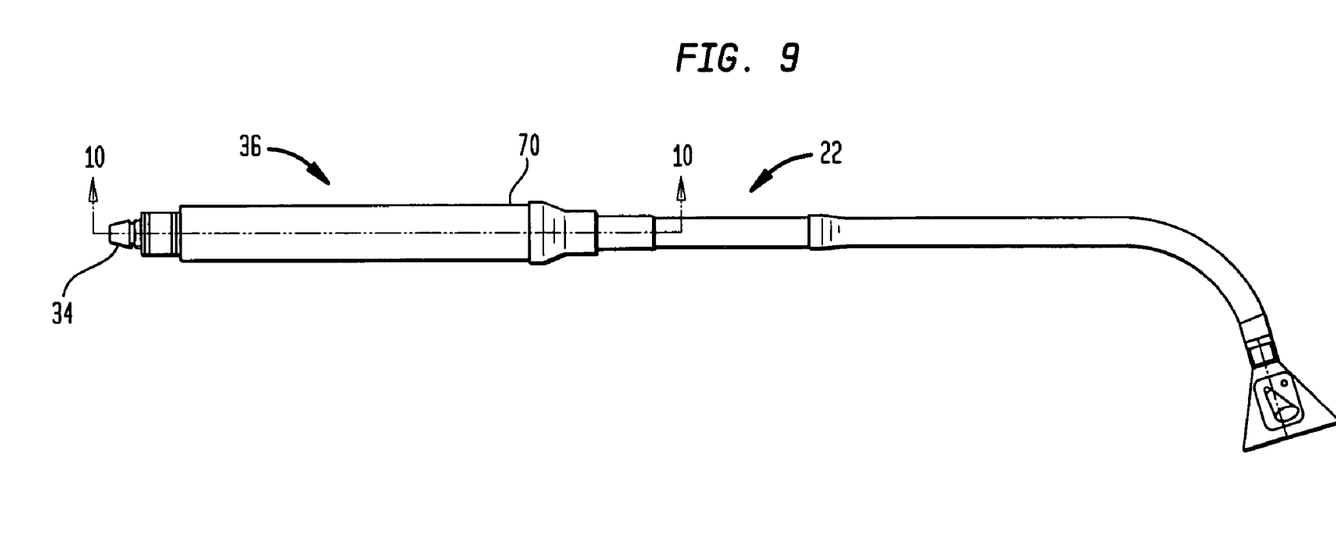
FIG. 9 is a side view of the phototherapy light with the outer spring assembly installed.
Figure 10:
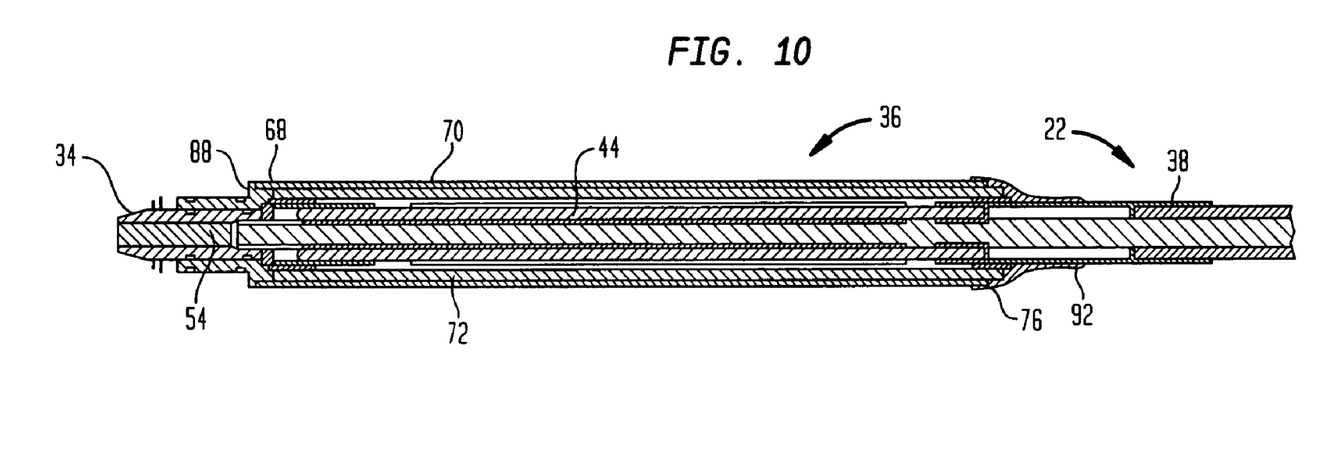
FIG. 10 is a cross-sectional view of the outer spring assembly taken along the line 10-10 of FIG. 9.

Turning finally to FIGS. 9 and 10, there is shown, respectively, a side view and a side cross sectional view, taken along the line 10-10 of FIG. 9, of the outer spring assembly 70 in its assembled position to make up the elongated neck 22. As can thus be seen, the outer spring assembly 70 has been slid over the proximal end 34 of the elongated neck 22 and is located at a position surrounding and general coaxial with the proximal inner spring 44. As such, the proximal flexible section 36 has the advantage of having both the outer spring 72 and the proximal inner spring 44 acting together to prevent the distal end 24 of the elongated neck 22 (FIG. 1) from sagging downwardly and also can provide protection against that sagging even in the event of a failure either the outer spring 72 or the proximal inner spring 44.

In order to position the outer spring assembly 70 in the proper position, the outer spring assembly 70 is slid onto the proximal end 34 of the elongated neck 22 until the shoulder 88 of the outer spring assembly 70 abuts against the shoulder 68 of the inner fitting 54 so that the outer spring assembly 70 fits firmly against inner fitting 54. At that point, the internal opening 92 of the distal fitting 76 has been dimensioned to slide tighty against the outer diameter of the intermediate tubing 38. That slippage may be enhanced by the presence of some lubricious material i.e wrapped Teflon, intermediate distal fitting 76 of the outer spring assembly 70 and the outer surface of the intermediate tubing 38 as well as having a polished surface on that outer surface.

Accordingly, as can now be appreciated, the elongated neck 22 can be directed by the user to the desired area of the infant. By the particular arrangement of the proximal flexible section and the distal flexible section the phototherapy light device 10 can be manipulated as desired, however, with the proximal flexible section having an inner proximal spring and an outer spring proximate to each other and generally coaxial, there is a safety factor in the event of a failure of either of those springs to prevent the distal end of the light therapy device from sagging downwardly to contact the infant.

Those skilled in the art will readily recognize numerous adaptations and modifications which can be made to the phototherapy light device of the present invention which will result in an improved phototherapy system for an infant care apparatus, yet all of which will fall within the scope and spirit of the present invention as defined in the following claims. Accordingly, the invention is to be limited only by the following claims and their equivalents.

We claim:

1. A phototherapy light device for treating infants, the phototherapy light device comprising a base, an elongated neck having a proximal end affixed to the base and a distal end, a light emanating device located at the distal end of the elongated neck, the elongated neck having a proximal gooseneck flexible section having opposite ends and a distal flexible section, an inflexible intermediate tubing located between the proximal gooseneck flexible section and the distal flexible section, the elongated neck further having an outer spring assembly comprising an outer coil spring having a distal fitting and a proximal fitting, wherein the outer coil spring encircles and is generally coaxial with the proximal gooseneck flexible section, the distal fitting and proximal fitting being located at the opposite ends of the proximal gooseneck flexible section, the distal fitting having an internal diameter dimensioned to allow the outer spring assembly to slide over the proximal gooseneck flexible section to secure the outer spring assembly to the elongated neck and to allow the outer spring assembly to be slidably removable from the proximal gooseneck flexible section, the proximal gooseneck flexible section and the distal flexible section supporting the light emanating device at the distal end of the elongated neck.

2. The phototherapy light device as defined in claim 1 wherein the light emanating device is a light producing device.

3. The phototherapy light device as defined in claim 1 wherein the elongated neck includes a distal tubing section extending from the distal flexible section to the distal end of the elongated neck.

4. The phototherapy light device as defined in claim 1 wherein the distal tubular section is curved.

5. The phototherapy light device as defined in claim 1 wherein the phototherapy light device comprises a light producing device located in the base and an optical fiber extends through the elongated neck to the light emanating device at the distal end of the phototherapy light device.

6. The phototherapy light device as defined in claim 1 wherein the outer spring assembly is slidingly received over the proximal gooseneck flexible section and is removable therefrom.

7. The phototherapy light device as defined in claim 1 wherein the elongated neck has an intermediate tubing extending between the proximal gooseneck flexible section and the distal gooseneck flexible section.

8. A infant care apparatus, said infant care apparatus comprising a frame structure forming an infant platform on which an infant is adapted to be positioned, the infant care apparatus having a phototherapy light device affixed to the frame structure, the phototherapy light device comprising a base, an elongated neck having a distal end extending from the base, a light emanating device located at the distal end of the elongated neck and a source of light to emanate from the light emanating device, the elongated neck having a distal flexible section, a proximal gooseneck flexible section having opposite ends and an intermediate inflexible tubing located between the distal flexible section and the proximal gooseneck flexible section, the proximal gooseneck flexible section having an outer spring assembly comprising an outer coil spring having a distal fitting and a proximal fitting, wherein the outer spring assembly encircles and is generally coaxial with the proximal flexible gooseneck section, the distal fitting and proximal fitting being located at the opposite ends of the proximal gooseneck flexible section, the distal fitting having an internal diameter dimensioned to allow the outer spring assembly to slide over the elongated neck to secure the outer spring assembly to the elongated neck and to allow the outer spring assembly to be slidably removable from the proximal gooseneck flexible section, the proximal gooseneck flexible section and the distal flexible section providing support to the light emanating device at the distal end of the elongated neck.

9. The infant care apparatus as defined in claim 8 wherein the device includes a source of light located in the base and an optical fiber system that transmits the light from the source of light to the light emanating device at the distal end of the elongated neck.

10. The infant care apparatus as defined in claim 8 wherein the infant care apparatus is an infant warmer.

11. The infant care apparatus as defined in claim 8 wherein the elongated neck includes a distal tubing extending from the distal flexible section to the distal end of the elongated neck and wherein the distal tubing is curved.

\* \* \* \* \*